(12) United States Patent
Cao et al.

(10) Patent No.: US 8,383,080 B2
(45) Date of Patent: Feb. 26, 2013

(54) TREATMENT OF CHA-TYPE MOLECULAR SIEVES AND THEIR USE IN THE CONVERSION OF OXYGENATES TO OLEFINS

(75) Inventors: Guang Cao, Branchburg, NJ (US); Matu J. Shah, Hackettstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1127 days.

(21) Appl. No.: 11/799,120

(22) Filed: May 1, 2007

(65) Prior Publication Data

US 2007/0286798 A1    Dec. 13, 2007

Related U.S. Application Data

(60) Provisional application No. 60/812,665, filed on Jun. 9, 2006.

(51) Int. Cl.
    *C01B 33/36*    (2006.01)
(52) U.S. Cl. .................................... 423/700; 423/702
(58) Field of Classification Search ........................ None
    See application file for complete search history.

(56) References Cited

U.S. PATENT DOCUMENTS

| | | | |
|---|---|---|---|
| 3,030,181 A | 4/1962 | Milton | |
| 3,493,519 A | 2/1970 | Kerr et al | |
| 4,326,994 A | 4/1982 | Haag et al. | |
| 4,544,538 A | 10/1985 | Zones | |
| 5,095,163 A | 3/1992 | Barger | |
| 6,709,644 B2 | 3/2004 | Zones et al. | |
| 7,094,389 B2 | 8/2006 | Cao et al. | |
| 7,148,172 B2 | 12/2006 | Strohmaier et al. | |
| 7,578,987 B2 * | 8/2009 | Wilson | 423/306 |

| | | | |
|---|---|---|---|
| 2003/0069449 A1 * | 4/2003 | Zones et al. | 564/463 |
| 2004/0116282 A1 * | 6/2004 | Mees et al. | 502/214 |
| 2005/0096494 A1 * | 5/2005 | Reyes et al. | 585/820 |
| 2005/0197520 A1 * | 9/2005 | Mertens et al. | 585/640 |

FOREIGN PATENT DOCUMENTS

| | | | |
|---|---|---|---|
| GB | 868846 | | 5/1961 |
| WO | WO 2005/063622 | * | 7/2005 |
| WO | WO 2006/057760 | * | 6/2006 |

OTHER PUBLICATIONS

"Water Saturation Pressure". The Engineering Tool Box. Http://www.engineeringtoolbox.com/water-vapor-saturation-pressure-d_599.html. Dec. 20, 2010.*
Mees, F.D.P, et al. "Improvement of the hydrothermal Stability of SAPO 34" Chem. Commun. 44-45 (2003).*
R.M.Barrer et al., "The Hydrothermal Chemistry of the Silicates, Synthetic Potassium Aluminosilicates," J. Chem. Soc., (1956), pp. 2882-2891.
Diaz-Cabanas et al.,"Synthesis and Structure of Pure SiO$_2$ Chabazite: the SiO$_2$ polymorph with the lowest framework density", Chem. Commun., pp. 1881-1882 (1998).

* cited by examiner

*Primary Examiner* — Melvin C Mayes
*Assistant Examiner* — Sheng H Davis
(74) *Attorney, Agent, or Firm* — David M. Weisberg; Kevin M. Faulkner (57) ABSTRACT

A method is disclosed of treating a crystalline material comprising a CHA framework-type molecular sieve, wherein said crystalline material has a composition and involving the molar relationship:

$$(n)X_2O_3{:}YO_2,$$

where X is a trivalent element, Y is a tetravalent element, and n is less than 0.07, and wherein the crystalline material does not comprise a silicoaluminophosphate, is substantially free of framework phosphorus, or both. The method can comprise treating the crystalline material with steam under conditions such that the prime olefin selectivity of the treated material in an oxygenate conversion process is greater than the prime olefin selectivity of the untreated material in the same process.

9 Claims, 3 Drawing Sheets

Figure 1. XRD Patterns of Products

Figure 2. SEM of Product A

Figure 3. MTO Performance

TREATMENT OF CHA-TYPE MOLECULAR SIEVES AND THEIR USE IN THE CONVERSION OF OXYGENATES TO OLEFINS

CROSS REFERENCE TO RELATED APPLICATION

This claims the benefit of and priority from U.S. Ser. No. 60/812,665, filed Jun. 9, 2006. The above application is fully incorporated herein by reference.

FIELD OF THE INVENTION

This invention relates to a method of treating chabazite framework-type molecular sieves and to the use of the treated sieves in the conversion of oxygenates to olefins.

BACKGROUND OF THE INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are 8-membered ring aluminosilicates, such as those having the chabazite (CHA) framework type, as well as silicoaluminophosphates of the CHA framework type, such as SAPO-34.

CHA framework-type molecular sieves appear to be particularly suitable catalysts for the OTO reaction since they have cages that are sufficiently large to accommodate aromatic intermediates while still allowing the diffusive transport of reactants and products into and out of the crystals through regularly interconnected window apertures. By complementing such morphological characteristics with appropriate levels of acid strength and acid density, working catalysts are produced. Extensive research in this area indicates that increasing the silica to alumina molar ratio seems to be a key requirement in the use of CHA framework-type aluminosilicates in OTO reactions.

Chabazite is a naturally occurring zeolite with the approximate formula $Ca_6Al_{12}Si_{24}O_{72}$. Three synthetic forms of chabazite are described in "Zeolite Molecular Sieves", by D. W. Breck, published in 1973 by John Wiley & Sons, the complete disclosure of which is fully incorporated herein by reference. The three synthetic forms reported by Breck are Zeolite "K-G", described in J. Chem. Soc., pg. 2822 (1956), Barrer et al; Zeolite D, described in British Patent No. 868,846 (1961); and Zeolite R, described in U.S. Pat. No. 3,030,181 (1962). Zeolite K-G zeolite has a silica:alumina mole ratio of 2.3:1 to 4.15:1, whereas zeolites D and R have silica:alumina mole ratios of 4.5:1 to 4.9:1 and 3.45:1 to 3.65:1, respectively. The relatively low silica to alumina molar ratio of these materials makes them less than optimal as catalysts for OTO reactions.

Considerable work has therefore been conducted on the synthesis of CHA framework-type aluminosilicate molecular sieves having high silica to alumina molar ratios and in particular with silica to alumina molar ratios greater than 15:1, preferably greater than 100:1.

For example, U.S. Pat. No. 4,544,538 describes the synthesis of a synthetic form of chabazite-type aluminosilicate, SSZ-13, using N-alkyl-3-quinuclidinol, N,N,N-tri-alkyl-1-adamantylammonium cations and/or N,N,N-trialkyl-exoaminonorbornane as a directing agent in a conventional $OH^-$ medium. According to the '538 patent, SSZ-13 typically has a silica to alumina molar ratio of 8 to 50 but it is stated that higher molar ratios can be obtained by varying the relative ratios of the reactants in the synthesis mixture and/or by treating the zeolite with chelating agents or acids to remove aluminum from the zeolite lattice. However, attempts to synthesize SSZ-13 in $OH^-$ media at silica to alumina molar ratios in excess of 100 have been unsuccessful and have produced ITQ-1 or SSZ-23, depending on the alkali metal cation present. Moreover, increasing the silica to alumina molar ratio of SSZ-13 by dealumination has met little or no success.

U.S. Pat. No. 6,709,644 describes a zeolite that is identified as SSZ-62 and has a CHA framework type and a crystal size of 0.5 microns or less. SSZ-62 is said to have a silica to alumina molar ratio in excess of 10, such as in excess of 30, but the only synthesis example produces a material with a silica to alumina molar ratio of 22. Synthesis is effected in a hydroxyl medium in the presence of N,N,N-trimethyl-1-adamantammonium cation as the structure directing agent. The zeolite can be steamed, purportedly to help stabilize the crystalline lattice to attack from acids.

An all silica crystalline molecular sieve having the CHA framework type has been hydrothermally synthesized using N,N,N-trimethyladamantylammonium in hydroxide form as the structure-directing agent, but the synthesis requires the presence of concentrated hydrofluoric acid. See Diaz-Cabanas, M-J, Barrett, P. A., and Camblor, M. A. "Synthesis and Structure of Pure $SiO_2$ Chabazite: the $SiO_2$ Polymorph with the Lowest Framework Density", Chem. Commun. 1881 (1998).

More recently, an aluminosilicate with the CHA framework type and having a silica to alumina molar ratio in excess of 100, such as from 150 to 2000, has been synthesized in the presence of fluoride ions. See U.S. Patent Application Publication No. 2003/0176751, published Sep. 18, 2003. Structure directing agents employed include N-alkyl-3-quinuclidinol, N,N,N-tri-alkyl-1-adamantammonium cations and N,N,N-trialkyl-exoaminonorbornane.

U.S. Published Patent Application No 2005/0154244, published Jul. 14, 2005, discloses a crystalline material comprising a CHA framework-type molecular sieve with stacking faults or at least one intergrown phase of a CHA framework-type molecular sieve and an AEI framework-type molecular sieve, wherein the material is substantially free of framework phosphorus and has a composition involving the molar relationship $(n)X_2O_3{:}YO_2$ wherein X is a trivalent element, Y is a tetravalent element and n is from 0 to about 0.5. The material can be synthesized using a mixed directing agent comprising an N,N,N-trialkyl-1-adamantylammonium compound and an N,N-diethyl-2,6-dimethylpiperidinium compound, normally in the presence of fluoride ions.

In pending US 2007-0100185 A1, we have described a method of synthesizing a crystalline material comprising a CHA framework-type molecular sieve, the method comprising: a) forming a reaction mixture capable of forming said crystalline material, wherein the reaction mixture comprises a structure directing agent having the formula:

$$[R^1R^2R^3N\text{—}R^4]^+Q^-$$

wherein $R^1$ and $R^2$ are independently selected from hydrocarbyl alkyl groups and hydroxy-substituted hydrocarbyl groups having from 1 to 3 carbon atoms, provided that $R^1$ and $R^2$ may be joined to form a nitrogen-containing heterocyclic structure, $R^3$ is an alkyl group having 2 to 4 carbon atoms and $R^4$ is selected from a 4- to 8-membered cycloalkyl group, optionally, substituted by 1 to 3 alkyl groups each having from 1 to 3 carbon atoms, and a 4- to 8-membered heterocyclic group having from 1 to 3 heteroatoms, said heterocyclic group being, optionally, substituted by 1 to 3 alkyl groups each having from 1 to 3 carbon atoms and each heteroatom in said heterocyclic group being selected from the group consisting of O, N, and S, or $R^3$ and $R^4$ are hydrocarbyl groups having from 1 to 3 carbon atoms joined to form a nitrogen-containing heterocyclic structure; and $Q^-$ is an anion; and b) recovering from said reaction mixture said crystalline material comprising a CHA framework-type molecular sieve.

Also, in pending US 2007-0100185 A1, we have described a method of synthesizing a crystalline material comprising a CHA framework-type molecular sieve and having a composition involving the molar relationship:

$$(n)X_2O_3{:}YO_2$$

wherein X is a trivalent element; Y is a tetravalent element; and n is from 0 to less than 0.01, such as from about 0.0005 to about 0.007, the method comprising: (a) preparing a reaction mixture capable of forming said material, said mixture comprising a source of water, a source of an oxide of a tetravalent element Y and, optionally, a source of an oxide of a trivalent element X, wherein the reaction mixture is substantially free of fluoride ions added as HF; (b) maintaining said reaction mixture under conditions sufficient to form crystals of said crystalline material; and (c) recovering said crystalline material.

Despite these synthesis advances, many of the resultant high silica CHA framework-type molecular sieves, and particularly those synthesized in the absence of HF, exhibit reduced MTO performance, such as an unexpectedly high selectivity to undesirable coke and methane. According to the invention, it has now been found that the MTO performance, and most importantly the prime olefin selectivity, of high silica CHA framework-type molecular sieves can be enhanced by mild steam treatment. Whereas the reason for this result is not fully understood, recent work has shown that many as-synthesized high silica CHA zeolites exhibit framework defects and it is believed that the steam treatment serves to heal these defects.

U.S. Pat. No. 4,326,994 discloses a method for increasing the catalytic activity of an acid zeolite having a determinable initial activity and characterized by a silica to alumina mole ratio of at least 12 and a constraint index within the approximate range of 1 to 12. The zeolite is selected from the group consisting of ZSM-5, ZSM-11, ZSM-12, ZSM-23, ZSM-35, and ZSM-38 and the activation method comprises contacting said zeolite with water for a sufficient treating time, temperature, and water partial pressure wherein said time, temperature and pressure is represented by the following relationship of treating time and water pressure at constant temperatures:

$$0.001(Pt)_T < (Pt) < 10(Pt)_T$$

where
$(Pt)_T = 2.6 \times 10^{-9}\ e\ 16000/T$
P=Water Partial Pressure, atmosphere
t=Treating Time, Hours
T=Temperature, °K.

U.S. Pat. No. 5,095,163 discloses a method of hydrothermal treatment of silicoaluminophosphate molecular sieves, such as SAPO-34, at temperatures in excess of about 700° C. for periods sufficient to destroy a large proportion of their acid sites while retaining at least 80 percent of their crystallinity. The hydrothermal treatment is found to result in a catalyst for converting methanol to lower olefins having increased catalyst life, increased selectivity for $C_2$ to $C_3$ olefins and decreased selectivity for paraffin production than the untreated SAPO-n starting composition.

Steaming is also known to be effective in the stabilization of large pore zeolites, such as zeolite Y. For example, U.S. Pat. No. 3,493,519 teaches a method of preparing ultrastable zeolite Y in which an ammonium form of zeolite Y is heated in the presence of rapidly flowing steam, and the resultant steamed product is base-exchanged with an ammonium salt and then treated with a chelating agent capable of combining with aluminum at a pH between 7 and 9. The steaming results in movement of mobile silicate species to defect sites, which is only possible with relatively large pore molecular sieves such as zeolite Y.

SUMMARY OF THE INVENTION

In one aspect, the present invention resides in a method of treating a crystalline material comprising a CHA framework-type molecular sieve, wherein said crystalline material has a composition substantially free of framework phosphorus and involving the molar relationship:

$$(n)X_2O_3{:}YO_2,$$

wherein X is a trivalent element, Y is a tetravalent element, and n is from 0 to less than 0.07, preferably from 0 to less than 0.02, and more preferably from 0 to less than 0.01, the method comprising treating said crystalline material with steam under conditions such that the prime olefin selectivity of the treated material in an oxygenate conversion process is greater than the prime olefin selectivity of the untreated material in the same process.

In a further aspect, the present invention resides in a method of synthesizing a crystalline material comprising a CHA framework-type molecular sieve and having a composition involving the molar relationship:

$$(n)X_2O_3{:}YO_2,$$

wherein X is a trivalent element, Y is a tetravalent element, and n is from 0 to less than 0.07, preferably from 0 to less than 0.02, and more preferably from 0 to less than 0.01, the method comprising:

(a) preparing a reaction mixture capable of forming said material, said mixture comprising a source of water, a source of an oxide of a tetravalent element Y and, optionally, a source of an oxide of a trivalent element X;

(b) maintaining said reaction mixture under conditions sufficient to form crystals of said crystalline material;

(c) recovering said crystalline material; and (d) contacting said crystalline material with an atmosphere containing steam at a temperature of about 400° C. to about 650° C. for a time of about 8 hours to about 170 hours.

Conveniently, the partial pressure of steam in said atmosphere is about 1 psia to about 25 psia (7 to 172 kPa).

Conveniently, the reaction mixture in (a) also comprises a source of alkali metal ions and the crystalline material recovered in (c) contains alkali metal.

Conveniently, the reaction mixture in (a) is substantially free of fluoride ions.

Preferably, the reaction mixture in (a) also comprises an organic directing agent for directing the synthesis of said CHA framework-type molecular sieve and the method includes removing the directing agent from the crystalline material recovered in (c). Conveniently, the directing agent is removed from the crystalline material recovered in (c) prior to contacting said crystalline material with said atmosphere containing steam.

In a further aspect, the invention resides in a process for producing olefins comprising contacting an organic oxygenate compound under oxygenate conversion conditions with a catalyst comprising a crystalline material treated or synthesized by the methods described herein.

DETAILED DESCRIPTION OF THE EMBODIMENTS

The present invention relates to a method of treating a high silica zeolite comprising a chabazite (CHA) framework-type molecular sieve so as to enhance its prime olefin selectivity. In this respect the term "prime olefin selectivity" (POS) is intended to mean the total selectivity to ethylene and propylene in the product obtained when the molecular sieve is used as a catalyst in an oxygenate-to-olefins conversion process. The treatment method includes contacting the molecular sieve with steam under relatively mild conditions. It is believed that the mild steam treatment heals defects in the crystal framework of the molecular sieve substantially without removing aluminum from the framework. The term "framework defects" means framework lattice sites that are vacated by silicon atoms. As a result of such vacancies hydroxyl groups terminate the broken bonds, as pictorially illustrated below:

Molecular Sieve

It is to be appreciated that molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the *Atlas of Zeolite Framework Types,* 5th edition, Elsevier, London, England (2001). Chabazite is one of the molecular sieves for which a structure has been established and materials of this framework type are designated as CHA.

In its calcined form, a high silica CHA-type molecular sieve, such as that employed in a treatment method of the present invention, has an X-ray diffraction pattern having the characteristic lines shown in Table 1.

TABLE 1

| d(Å) | Relative Intensities 100 I/I$_o$ |
|---|---|
| 9.36-8.98 | 80-100 |
| 6.86-6.66 | 20-60 |
| 6.33-6.15 | 0-10 |
| 5.51-5.38 | 5-40 |
| 4.97-4.86 | 5-50 |
| 4.63-4.54 | 0-10 |
| 4.28-4.20 | 20-60 |
| 3.94-3.87 | 0-10 |
| 3.83-3.76 | 0-10 |
| 3.54-3.49 | 5-40 |
| 3.41-3.36 | 5-40 |
| 3.14-3.10 | 0-10 |
| 2.889-2.853 | 5-50 |
| 2.850-2.815 | 5-40 |
| 2.650-2.620 | 0-10 |
| 2.570-2.542 | 0-10 |
| 2.467-2.441 | 0-10 |
| 2.244-2.223 | 0-10 |
| 2.088-2.070 | 0-10 |
| 2.059-2.041 | 0-10 |
| 1.883-1.869 | 0-10 |
| 1.842-1.828 | 0-10 |

These X-ray diffraction data were collected with a Philips powder X-Ray Diffractometer, equipped with a scintillation detector with graphite monochromator, using copper K-alpha radiation. The diffraction data were recorded by step-scanning at 0.02 degrees of two-theta, where theta is the Bragg angle, and a counting time of 1 second for each step. The interplanar spacing, d's, were calculated in Angstrom units, and the relative intensities of the lines, (where I/I$_o$ is one-hundredth of the intensity of the strongest line), above background were determined by integrating the peak intensities. It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the framework atom connectivities. These minor effects, including changes in relative intensities, can also occur as a result of differences in cation content, framework composition, nature and degree of pore filling, crystal size and shape, preferred orientation and thermal and/or hydrothermal history.

CHA framework-type molecular sieves and other regular crystalline solids are built from structurally invariant building units, called Periodic Building Units, and are periodically ordered in three dimensions. Structurally disordered struc- tures are also known and show periodic ordering in dimensions less than three, i.e., in two, one, or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

In the case of a regular CHA framework-type molecular sieve, the Periodic Building Unit is a double 6-ring layer. There are two types of layers "a" and "b", which are topologically identical except "b" is the mirror image of "a". When layers of the same type stack on top of one another, i.e., aaaaaaaa or bbbbbbbb, the framework-type CHA is generated. When layers "a" and "b" alternate, i.e., abababab, a different framework type, AEI, is generated. Intergrown CHA/AEI molecular sieves comprise regions of CHA framework-type sequences and regions of AEI framework-type sequences. Each change from a CHA to an AEI framework-type sequence results in a stacking fault. In addition, stacking faults can occur in a pure CHA-phase material when a sequence of one mirror image layers intersects a sequence of the opposite mirror image layers, such as, for example, in aaaaaabbbbbb.

AEI framework-type molecular sieves exhibit a different X-ray diffraction pattern from CHA framework-type materials. Thus, analysis of intergrown molecular sieves, such as AEI/CHA intergrowths, can be effected by X-ray diffraction and, in particular, by comparing the observed patterns with calculated patterns generated using algorithms to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499-520). DIFFaX is the simulation program selected by and available from the International Zeolite Association to simulate the XRD powder patterns for randomly intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA, and KFI, as reported by K. P. Lillerud et al. in "Studies in Surface Science and Catalysis", 1994, Vol. 84, pp. 543-550.

The crystalline material employed in the treatment method of the present invention comprises a CHA framework-type molecular sieve, either alone as a pure phase material, or in the presence of stacking faults or including at least one intergrown phase of a CHA framework-type molecular sieve with a different phase, such as an AEI framework-type molecular sieve. In its calcined and anhydrous form, the material preferably does not comprise a silicoaluminophosphate and/or is substantially free of framework phosphorus and has a composition involving the following molar relationship:

wherein X (if present) is a trivalent element, such as aluminum, boron, iron, indium, gallium or a combination thereof, typically aluminum; Y is a tetravalent element, such as silicon, tin, titanium, germanium, or a combination thereof, typically silicon; and n is from 0 to less than 0.07, preferably from 0 to less than 0.02, and more preferably from 0 to less than 0.01.

As used herein, the phrase "substantially free," with regard to a component in a composition, should be understood to mean that the composition contains less than about 5 wt %, preferably less than about 1 wt %, more preferably less than about 0.1 wt %, for example less than about 0.05 wt %, or completely none, of the component.

In its as-synthesized form, the crystalline material treated by the method of the present invention has a composition involving the molar relationship:

wherein X, Y, and n are as defined in the preceding paragraph, R is at least one organic directing agent and M is an alkali metal and wherein m ranges from about 0.01 to about 2, such as from about 0.1 to about 1, y ranges from about 0 to about 0.07, such as from about 0 to about 0.02, z ranges from about 0.5 to about 100, such as from about 2 to about 20 and x ranges from about 0 to about 2, such as from about 0 to about 1. Preferably, x is zero. The R and M components and, if present, the F component are associated with the material as a result of their presence during crystallization and can be at least partly removed by post-crystallization methods hereinafter more particularly described.

Molecular Sieve Synthesis

High silica CHA-containing zeolites can be prepared from a reaction mixture containing a source of water, a source of an oxide of the tetravalent element Y, optionally, a source of an oxide of the trivalent element X, and at least one organic directing agent (R) as described below. Preferably, the reaction mixture is substantially free of fluoride ions, although in some cases fluoride ions may be present particularly where added as neutral fluoride salts, for example, of the directing agent (R). Useful and typical ranges for the composition, in terms of mole ratios of oxides, of the reaction mixture are given in Table 2.

TABLE 2

| Reactants | Useful | Typical |
| --- | --- | --- |
| H$_2$O/YO$_2$ | 0.1 to 40 | 5 to 30 |
| Fluoride/YO$_2$ | 0 to 2 | 0 to 1 |
| R/YO$_2$ | 0.01 to 2 | 0.1 to 1 |
| X$_2$O$_3$/YO$_2$ | 0 to 0.02 | 0.0005 to 0.007 |

In addition, the reaction mixture will normally also contain alkali metal (M) cations added as part of the sources of the oxides X$_2$O$_3$ and/or YO$_2$. Typically, the molar ratio of M$_2$O/YO$_2$ is between about 0 and about 0.07.

Where the tetravalent element Y is silicon, suitable sources of silicon include silicates, e.g., tetraalkyl orthosilicates, fumed silica, such as Aerosil (available from Degussa), and aqueous colloidal suspensions of silica, for example, that sold by E.I. du Pont de Nemours under the tradename Ludox. Where the trivalent element X is aluminum, suitable sources of aluminum include aluminum salts, especially water-soluble salts, such as aluminum nitrate, as well as hydrated aluminum oxides, such as boehmite and pseudoboehmite. Where the halide is fluoride, suitable sources of fluoride include hydrogen fluoride, although more benign sources of fluoride such as alkali metal fluorides and fluoride salts of the organic directing agent are preferred.

Suitable organic directing agents R for directing the synthesis of a CHA framework-type material include adamantammonium compounds, such as N,N,N-trimethyl-1-adamantammonium compounds, N,N,N-trimethyl-2-adamantammonium compounds, and N,N,N-trimethylcyclohexylammonium compounds, N,N-dimethyl-3,3-dimethylpiperidinium compounds, N,N-methylethyl-3,3-dimethylpiperidinium compounds, N,N-dimethyl-2-methylpiperidinium compounds, 1,3,3,6,6-pentamethyl-6-azonio-bicyclo(3.2.1)octane compounds, N,N-dimethylcyclohexylamine, and the bi- and tri-cyclic nitrogen containing organic compounds cited in: (1) *Zeolites and Related Microporous Materials*: State of the Art 1994, Studies of Surface Science and Catalysis, Vol. 84, pp. 29-36; (2) *Novel Materials in Heterogeneous Catalysis* (ed. Terry K. Baker & Larry L. Murrell), Chapter 2, pp. 14-24, May 1990; (3) J. Am. Chem. Soc., 2000, 122, pp. 263-273; and (4) U.S. Pat. Nos. 4,544,538 and 6,709,644. Suitable compounds include hydroxides and salts, such as neutral halides, for example, chlorides and fluorides.

Alternatively, the organic directing agent R used herein to direct the formation of a CHA framework-type molecular sieve is a cyclic ammonium compound having the formula:

$$[R^1R^2R^3N-R^4]^+Q^-$$

wherein

$R^1$ and $R^2$ are independently selected from hydrocarbyl groups and hydroxy-substituted hydrocarbyl groups having from 1 to 3 carbon atoms, provided that $R^1$ and $R^2$ may be joined to form a nitrogen-containing heterocyclic structure, $R^3$ is an alkyl group having 2 to 4 carbon atoms and $R^4$ is selected from a 4- to 8-membered cycloalkyl group, optionally, substituted by 1 to 3 alkyl groups each having from 1 to 3 carbon atoms; and a 4- to 8-membered heterocyclic group having from 1 to 3 heteroatoms, said heterocyclic group being, optionally, substituted by 1 to 3 alkyl groups each having from 1 to 3 carbon atoms and each heteroatom in said heterocyclic group being selected from the group consisting of O, N, and S, or

$R^3$ and $R^4$ are hydrocarbyl groups having from 1 to 3 carbon atoms joined to form a nitrogen-containing heterocyclic structure; and $Q^-$ is an anion, such as hydroxide or halide.

In one embodiment, $R^4$ is a cyclohexyl group, $R^1$ and $R^2$ are independently selected from a methyl group and an ethyl group and $R^3$ is an ethyl group. In this embodiment, preferred $[R^1R^2R^3N-R^4]^+$ cations include N,N,N-dimethylethylcyclohexylammonium (DMECHA):

N,N,N-methyldiethylcyclohexylammonium (MDECHA):

and N,N,N-triethylcyclohexylammonium (TECHA):

In another embodiment, $R^1$ and $R^2$ are joined to form a substituted or unsubstituted 5-membered nitrogen-containing heterocyclic ring. Conveniently, $R^3$ and $R^4$ are hydrocarbyl groups joined to form a substituted or unsubstituted 6-membered nitrogen-containing heterocyclic ring. In this embodiment, a preferred $[R^1R^2R^3N-R^4]^+$ cation includes 2,7-dimethyl-1-azonium[5,4]decane (DM27AD):

In addition to the organic directing agent for directing the formation of a CHA framework-type molecular sieve, the reaction mixture may also comprise a further organic directing agent for directing the formation of an AEI framework-type molecular sieve. In this case, the resultant crystalline material will tend to contain either stacking faults or at least one intergrown phase of a CHA framework-type molecular sieve and an AEI framework-type molecular sieve. Conveniently, said further organic directing agent comprises a monocyclic amine or ammonium compound, such as a substituted piperidine or piperidinium compound, for example, a tetraalkylpiperidinium compound, typically an N,N-diethyl-2,6-dimethylpiperidinium compound.

Typically, the reaction mixture also contains seeds to facilitate the crystallization process. The amount of seeds employed can vary widely, but generally the reaction mixture comprises from about 0.1 ppm by weight to about 10,000 ppm by weight, such as from about 100 ppm by weight to about 5,000 by weight, of said seeds. Conveniently, the seeds comprise a crystalline material having an AEI, LEV, CHA, ERI, AFX, or OFF framework-type molecular sieve. The seeds may be added to the reaction mixture as a colloidal suspension in a liquid medium, such as water. The production of colloidal seed suspensions and their use in the synthesis of molecular sieves are disclosed in, for example, International Publication Nos. WO 00/06493 and WO 00/06494 published on Feb. 10, 2000, which are fully incorporated herein by reference.

Conveniently, the reaction mixture has a pH of about 4 to about 14, such as about 5 to about 13, for example, about 6 to about 12.

Crystallization can be carried out at either static or stirred conditions in a suitable reactor vessel, such as, for example, polypropylene jars or Teflon®-lined or stainless steel autoclaves, at a temperature of about 120° C. to about 220° C., such as about 140° C. to about 200° C., for a time sufficient for crystallization to occur. Formation of the crystalline product can take anywhere from around 30 minutes up to as much as 2 weeks, such as from about 45 minutes to about 240 hours, for example, from about 1.0 to about 120 hours. The duration depends on the temperature employed, with higher temperatures typically requiring shorter hydrothermal treatments.

Typically, the crystalline product is formed in solution and can be recovered by standard means, such as by centrifugation or filtration. The separated product can also be washed, recovered by centrifugation or filtration and dried. The resultant product is found to comprise particles with an average crystal size below 4 microns, such as below 2 microns and typically about 0.5 microns.

As a result of the crystallization process, the recovered crystalline product contains within its pores at least a portion of the organic directing agent used in the synthesis. In a preferred embodiment, the organic directing agent is removed from the molecular sieve, leaving the catalytic sites within the microporous channels of the molecular sieve open for contact with a feedstock. Removal of the organic is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by conventional desorption processes.

To the extent desired and depending on the $X_2O_3/YO_2$ molar ratio of the material, any cations, particularly alkali metal cations, in the as-synthesized CHA framework-type material can be replaced in accordance with techniques well known in the art, at least in part, by ion exchange with other cations. Preferred replacing cations include metal ions, hydrogen ions, hydrogen precursor, e.g., ammonium ions, and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB, and VIII of the Periodic Table of the Elements.

Once the CHA framework-type containing material of the invention has been synthesized, it can be formulated into a catalyst composition by combination with other materials, such as binders and/or matrix materials, that provide additional hardness or catalytic activity to the finished catalyst.

Materials which can be blended with the CHA framework-type containing material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of zeolitic material contained in the final catalyst product ranges from 10 to 90 weight percent of the total catalyst, preferably 20 to 70 weight percent of the total catalyst.

Steaming of the Molecular Sieve

In accordance with the invention, the high silica CHA framework-type molecular sieve described above is subjected to a mild steaming treatment so as to enhance its selectivity for the production of prime olefins when used in an oxygenate-to-olefin conversion process. In one embodiment, the enhancement in prime olefin selectivity can be an increase of at least about 2%, preferably at least about 4%.

The steaming is typically conducted at a temperature of about 400° C. to about 650° C., preferably about 450° C. to about 600° C., for a time of about 8 hours to about 170 hours, preferably about 10 hours to about 120 hours using an atmosphere containing steam at a partial pressure of about 1 psia to about 25 psia (7 to 172 kPa), preferably about 2 psia to about 15 psia (14 to 103 kPa).

It is believed that the steaming heals defects in the framework structure of the molecular sieve, but it is important that the steaming is not so severe as to effect significant removal of the aluminum from the framework structure. Thus, as the steaming temperature is increased towards the upper ends of the ranges given above, it is to be appreciated that one or both of the steaming time and steam partial pressure should be decreased toward the lower ends of their respective ranges.

The steaming can be conducted on the as-synthesized molecular sieve (containing the directing agent and the alkali metal cations remaining from the synthesis) or, more preferably, can be conducted after one or both of the directing agent and the alkali metal cations have been partially or completely removed by post-synthesis treatments.

Uses of the Treated Molecular Sieve

The crystalline material treated by the method of the invention can be used to dry gases and liquids; for selective molecular separation based on size and polar properties; as an ion-exchanger; as a chemical carrier; in gas chromatography; and as a catalyst in organic conversion reactions. Examples of suitable catalytic uses of the crystalline material produced by the method of the invention include: (a) hydrocracking of heavy petroleum residual feedstocks, cyclic stocks and other hydrocrackate charge stocks, normally in the presence of a hydrogenation component is elected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes; (j) catalytic reduction of nitrogen oxides; and (k) synthesis of monoalkylamines and dialkylamines.

In particular, however, the crystalline material treated by the method of the invention is useful in the catalytic conversion of oxygenates to one or more olefins, particularly ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally, with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example, from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example, in the range of from about 0.1 $hr^{-1}$ to about 200 $hr^{-1}$.

A practical embodiment of a reactor system for the oxygenate conversion process is a circulating fluid-bed reactor with continuous regeneration, similar to a modern fluid catalytic cracker. Fixed beds are generally not preferred for the process because oxygenate-to-olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example, air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$-$C_4$ aldehyde composition and/or a $C_4$-$C_7$ olefin composition to form an integrated hydrocarbon co-catalyst within the porous framework of the CHA framework-type molecular sieve prior to the catalyst being used to convert oxygenate to olefins. Desirably, the pretreatment is conducted at a temperature of at least 10° C., such as at least 25° C., for example, at least 50° C., higher than the temperature used for the oxygenate reaction zone and is arranged to produce at least 0.1 wt %, such as at least 1 wt %, for example, at least about 5 wt % of the integrated hydrocarbon co-catalyst, based on total weight of the molecular sieve. Such preliminary treating to increase the carbon content of the molecular sieve is known as "pre-pooling" and is further described in U.S. Pat. Nos. 7,045,672; 7,057,083; and 7,132,581; all of which are fully incorporated herein by reference.

EXAMPLES

The invention will now be more particularly described with reference to the following Examples. In the Examples, X-ray Powder Diffractograms were recorded on a Siemens D500 diffractometer with voltage of 40 kV and current of 30 mA, using a Cu target and Ni-filter ($\lambda$=0.154 nm). Elemental analysis of Al, Si, and P was performed using Inductively Coupled Plasma (ICP) spectroscopy.

Example 1

Synthesis of High-Silica Chabazite (without the Use of Fluoride)

42.72 g of a 11.9 wt % aqueous solution of N,N,N-trimethyladamantammonium hydroxide (TMAAOH) was added to 9.24 g deionized water and then 8.04 g of Hi-Sil® 233 silica (PPG Industries, USA) was added to the mixture. The mixture was stirred until a uniform gel was produced. The Hi-Sil® 233 silica contained 0.53 wt % Na, 0.01 wt % K, 0.42 wt % alumina, and 82.2 wt % silica (Si/Al ratio of the material is 164) and hence the gel composition was as follows:

0.2 TMAA: (1/120)Na$_2$O: (1/328)Al$_2$O$_3$: 1.0SiO$_2$: 22H$_2$O

The gel into four equal portions, designated A to D respectively, and each portion was crystallized as follows.

Portion A was aged at room temperature for 2 hours before 200 PPM colloidal LEV seeds (14 wt % solid content, Si/Al=6 for the sieve) based on the weight of gel were added. The resultant mixture was sealed in a 23-mL Teflon-lined Parr autoclave and was heated in a 170° C. oven for three days while being tumbled at 40 rpm.

Portion B was aged for two days at room temperature until the pH had dropped from 13 to 11. The same amount of seeds as used with portion A was added with thorough mixing. The uniform gel was sealed in a 23-mL Teflon-lined Parr autoclave and was heated in a 170° C. oven for three days while being tumbled at 40 rpm.

Portions C and D were not aged, nor were seeds added thereto. They were individually sealed in 23-mL Teflon-lined Parr autoclaves and were heated in a 170° C. oven for 5 and 9 days, respectively, with no agitation.

The solid products were isolated and cleaned by centrifugation and washing with deionized water until the conductivity of the washings was lower than 50 mS/cm. The solid products were dried in a 50° C. vacuum oven overnight.

Figure 1:
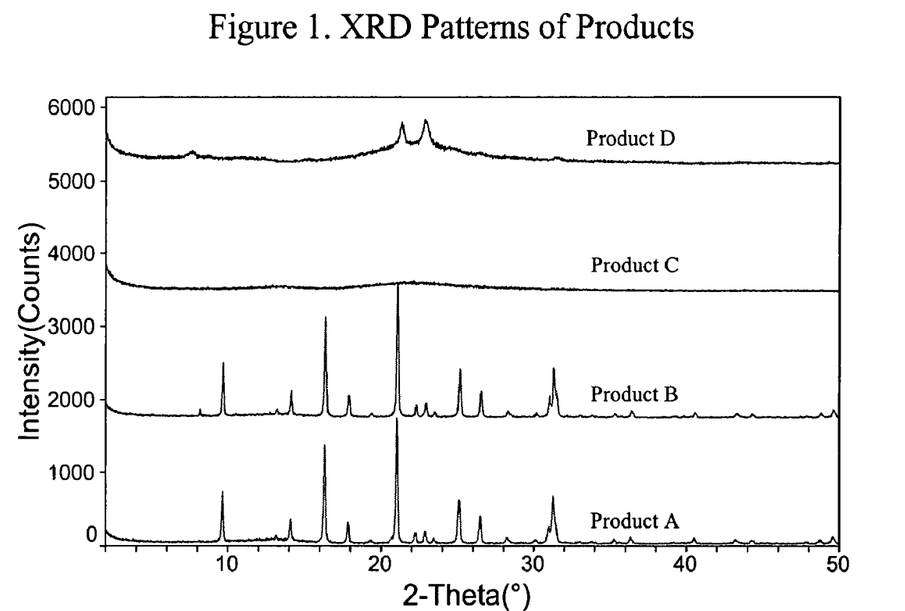
FIG. 1 provides X-ray diffraction patterns of the as-synthesized products A to D of Example 1.

The XRD patterns of the products are shown in FIG. 1. It can be seen that product A appears to be pure chabazite (1.65 g product recovered, 11.8% yield based on the weight of the gel), while product B had a trace amount of unidentified crystalline impurity. Products C and D were amorphous and nearly amorphous, respectively.

Figure 2:
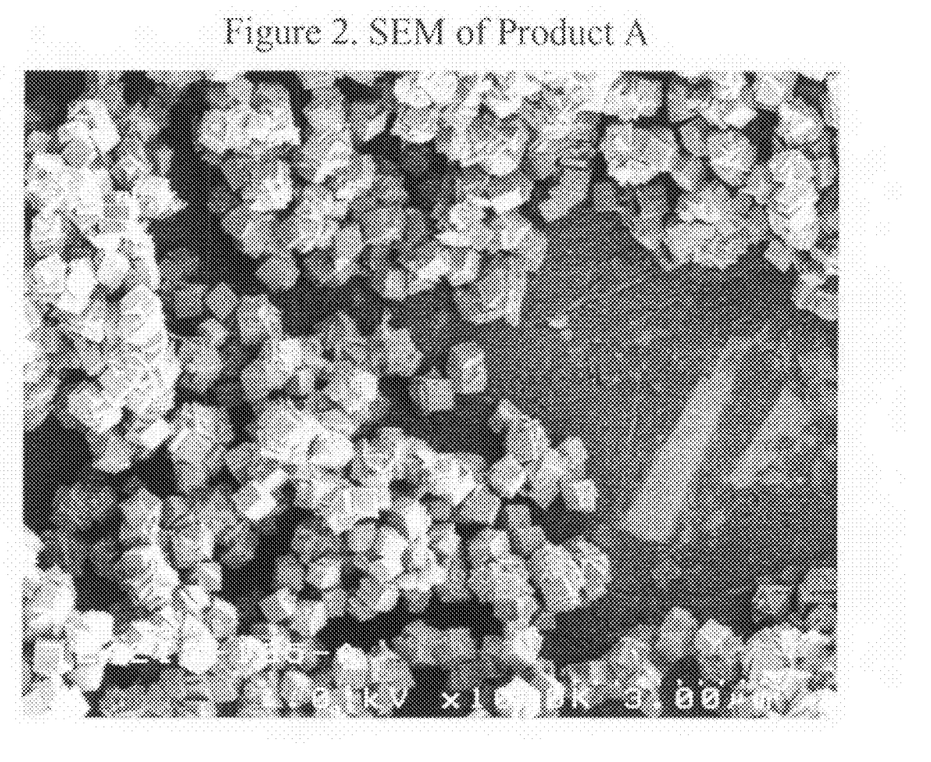
FIG. 2 is an SEM picture of product A of Example 1.

The SEM of Product A is shown in FIG. 2, indicating that no impurity phases were visible and the chabazite crystals were mostly twinned cubes of approximately 0.5 μm in size.

Elemental analysis yielded the following data for Product A (in wt %): Na, 0.067; Al$_2$O$_3$, 0.42; SiO$_2$, 72.1, which corresponded to Na$_{0.35}$Al$_{1.00}$Si$_{143}$.

Example 2

Calcination and NH$_4$-Exchange

Product A was calcined using the following protocol: (a) ramp at 10° C./min to 400° C. under flowing nitrogen and dwell for 30 minutes; (b) switch to flowing air and resume temperature ramp at 10° C./min to 650° C. and dwell at 650° C. for 4 hours. The calcined sample was ion-exchanged twice with 5 wt % ammonium chloride solution. Elemental analysis yielded the following data for the calcined and exchanged sample (in wt %): Na, 0.0125; Al$_2$O$_3$, 0.531; and SiO$_2$, 84.4, which corresponded to Na$_{0.05}$Al$_{1.00}$Si$_{34}$.

Example 3

Mild-Steaming

The calcined and NH$_4$-exchanged sample from Example 2 was loaded into two frit-bottomed quartz tubes. The tubes were placed on the frit of a larger diameter quartz tube, with the frit located at the middle of the tube. The large tube, along with the two smaller tubes was vertically positioned inside a tube furnace. From the bottom of the large tube, nitrogen alone or nitrogen with steam in 660:100 molar ratio was fed into the tube. The total pressure was atmospheric. The temperature was ramped to 500° C. at 10° C./min rate while the nitrogen feed was continued. After the temperature had stabilized at 500° C., feeding of nitrogen with steam commenced. The first sample was retrieved after steaming for 48 hours and the second after 96 hours. These samples, along with the unsteamed sample made in Example 2, were tested for MTO performance.

Example 4

MTO Testing

The Methanol-To-Olefins reaction was carried out in a fixed-bed microreactor. Methanol was fed at a preset pressure and rate to a stainless steel reactor tube housed in an isothermally heated zone. The reactor tube contained about 20 mg weighed and sized granules of the catalyst sample (20-40 mesh by press-and-screen method). The catalyst was activated for 30 minutes at 500° C. in flowing nitrogen before methanol was admitted. The product effluent was sampled, at different times during the run, with a twelve-port sampling loop while the catalyst was continuously deactivating. The effluent sample in each port was analyzed with a Gas Chromatograph equipped with an FID detector. The amount of coke on the catalysts at the end of the MTO test was determined by measuring the weight loss of the sample in air in a TGA unit between 300 and 650° C. (10° C./min ramp rate).

The testing conditions were as follows: the temperature was 540° C. and the pressure of methanol was 40 psia. The feed rate in weight hourly space velocity (WHSV) was 100/h. Cumulative conversion of methanol was expressed as grams of methanol converted per gram of sieve catalyst (CMCPS). On-stream lifetime refers to the CMCPS when methanol conversion has dropped to 10%. The product selectivities are reported as averages over the entire conversion range, rather than from a single point in effluent composition.

Figure 3:
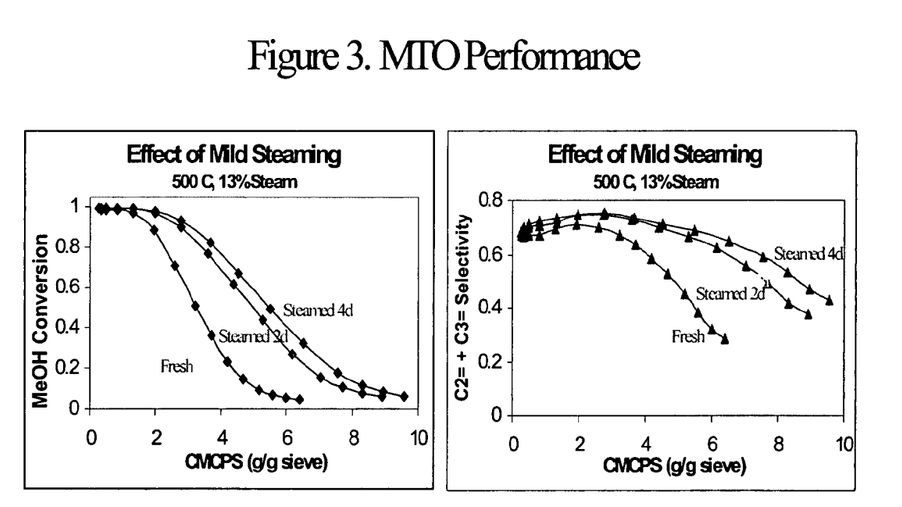
FIG. 3 provides graphs of the methanol conversion activity and the selectivity to ethylene plus propylene of product A, before and after steaming by the process of Example 3.

The results are summarized in FIG. 3, from which it is clear that both the on-stream lifetime and the prime olefin selectivity improved with increasing time of steaming. There was no indication that steaming had caused decrease in activity. Table 3 shows selectivity of key MTO products.

TABLE 3

| Catalyst | Parent HiSi-CHA | Steamed 2 days | Steamed 4 days |
|---|---|---|---|
| Total MeOH converted, g MeOH/g Sieve | 6.42 | 8.92 | 9.57 |
| Initial Conversion, % | 99.1 | 99.5 | 99.4 |
| C$_2$= + C$_3$= | 64.7 | 66.2 | 67.8 |
| C$_2$=/C$_3$= | 1.11 | 1.16 | 1.16 |
| CH$_4$ | 7.65 | 7.36 | 6.51 |
| C$_3$H$_8$ | 0.44 | 0.44 | 0.42 |
| End of Run Coke | | 9.3% on sieve | 6.3% on sieve |

Table 3 clearly shows that mild steaming caused MTO performance to improve in almost every measure, including an increase in the selectivity to ethylene plus propylene and decreases in the selectivity for methane and coke.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of synthesizing a crystalline material comprising a CHA framework-type molecular sieve and having a composition involving the molar relationship:

$$(n)X_2O_3:YO_2,$$

wherein X is a trivalent element, Y is a tetravalent element, and n is less than 0.07, the method comprising:
 (a) preparing a reaction mixture capable of forming said material, said mixture comprising a source of water, a source of an oxide of a tetravalent element Y, an organic directing agent and, optionally, a source of an oxide of a trivalent element X;
 (b) maintaining said reaction mixture under conditions sufficient to form crystals of said crystalline material; wherein the mixture is aged at about room temperature from about 30 minutes to about 120 hours before colloidal LEV seeds are added, followed by heating the mixture while tumbling at a temperature of about 140° C. to about 200° C. for about 1 to about 120 hours to form said crystalline material;
 (c) recovering said crystalline material and removing the directing agent from the recovered crystalline material; and
 (d) contacting said crystalline material with an atmosphere containing steam at a temperature of about 400° C. to about 650° C. for a time of about 8 hours to about 170 hours, said atmosphere comprises a steam partial pressure of about 1 psia to about 25 psia (7 to 172 kPa);
 wherein the directing agent is removed from the crystalline material recovered in (c) prior to contacting said crystalline material with said atmosphere containing steam.

2. The method of claim 1, wherein the reaction mixture in (a) is substantially free of all fluoride ions.

3. The method of claim 1, wherein the reaction mixture in (a) also comprises a source of alkali metal ions and the crystalline material recovered in (c) contains alkali metal.

4. The method of claim 1, wherein n is less than 0.02.

5. The method of claim 1, wherein n is less than 0.01.

6. The method of claim 1, wherein Y is silicon, tin, titanium, germanium, or a combination thereof.

7. The method of claim 1, wherein Y is silicon.

8. The method of claim 1, wherein X is aluminum, boron, iron, indium, gallium, or a combination thereof.

9. The method of claim 1, wherein X is aluminum.

* * * * *